(12) United States Patent  
Dort

(10) Patent No.: US 7,533,674 B2
(45) Date of Patent: May 19, 2009

(54) TONGUE RETENTION DEVICE

(76) Inventor: Leslie Dort, Box 2, Site 31 RR12, Calgary, Alberta (CA) T3E 6W3

(*) Notice: Subject to any disclaimer, the term of this patent is extended or adjusted under 35 U.S.C. 154(b) by 175 days.

(21) Appl. No.: 10/084,232

(22) Filed: Feb. 28, 2002

(65) Prior Publication Data
US 2002/0117178 A1 Aug. 29, 2002

Related U.S. Application Data

(60) Provisional application No. 60/272,433, filed on Feb. 28, 2001.

(51) Int. Cl.
A61C 5/14 (2006.01)
(52) U.S. Cl. .................. 128/859; 128/860; 128/861
(58) Field of Classification Search .......... 128/846, 128/848, 859–862; 602/902; 433/6–8
See application file for complete search history.

(56) References Cited

U.S. PATENT DOCUMENTS

| 3,809,094 | A |   | 5/1974  | Cook |
| 4,169,473 | A |   | 10/1979 | Samelson |
| 4,196,724 | A |   | 4/1980  | Wirt et al. |
| 4,198,967 | A |   | 4/1980  | Dror |
| 4,304,227 | A |   | 12/1981 | Samelson |
| 4,676,240 | A |   | 6/1987  | Gardy |
| 5,020,529 | A | * | 6/1991  | Gobin ................... 128/202.28 |
| 5,318,043 | A | * | 6/1994  | Burr et al. .................. 128/859 |
| 5,373,859 | A | * | 12/1994 | Forney ..................... 128/846 |
| 5,390,681 | A | * | 2/1995  | Daley ...................... 128/842 |
| 5,465,734 | A | * | 11/1995 | Alvarez .................... 128/848 |
| 5,570,702 | A | * | 11/1996 | Forman .................... 128/842 |
| 5,649,540 | A |   | 7/1997  | Alvarez et al. |
| 5,664,946 | A | * | 9/1997  | Bedi ........................ 433/140 |
| 6,494,209 | B2 | * | 12/2002 | Kulick ....................... 128/848 |
| 6,536,424 | B2 | * | 3/2003  | Fitton ..................... 128/200.24 |
| 6,877,513 | B2 | * | 4/2005  | Scarberry et al. ............. 128/848 |
| 7,073,506 | B2 |   | 7/2006  | Robertson et al. |

* cited by examiner

Primary Examiner—Michael A. Brown
(74) Attorney, Agent, or Firm—Bennett Jones LLP

(57) ABSTRACT

A device for retaining a tongue in a predetermined position, the device comprising, a flange having a first and second surface, the flange further including a protrusion extending from the first surface of the flange; and an aperture formed through the first and second surfaces of the flange, wherein the protrusion covers the aperture, whereby the protrusion form a hollow chamber, the hollow chamber is accessible through the aperture from the second side of the flange.

25 Claims, 6 Drawing Sheets

TONGUE RETENTION DEVICE

This application claims the benefit of U.S. Provisional Application Ser. No. 60/272,433 filed Feb. 28, 2001.

FIELD OF THE INVENTION

The present invention relates to dental devices for treating snoring and sleep apnea, more particularly the present invention relates to devices for positioning and restraining the tongue of a person.

RELATED ART

Many studies have been undertaken to better understand snoring and sleep apnea. It has been well documented that snoring occurs while breathing through the mouth during sleep when the tongue partially blocks the airway. Thus, one way to cure or mitigate snoring is to hold the tongue in a forward position, whereby airway blockage cannot occur. Although generally merely an annoyance to those other than the person snoring, it is known that in certain instances airway blockage will become complete resulting in apnea, i.e., a cutting off of the air supply to the lungs and thus decreasing the amount of oxygen carried by the blood to the brain.

Sleep apnea not only interrupts a persons sleep patterns resulting in chronic fatigue, it can also cumulatively cause brain damage. Therefore, for many persons, reducing or eliminating snoring is a serious matter. Sleep apnea can be classified into three basic categories, 1.) Central apnea, 2.) Obstruction Apnea, and 3.) Mixed Apnea.

Central apnea is classified as a stoppage of airflow because inspiratory efforts temporarily cease. The airway remains open and the chest walls make no effort to create airflow. The potential medical effects which may result due to central apnea are: encephalitis, brainstem neoplasm, brain stem infarction, poliomyelitis, spinal cord injury, and cervical cordoromy.

Obstruction apnea is classified as the cessation of airflow due to total airway collapse despite a persistent effort to breath. An obstruction in the upper airway can occur in three areas which are, a.) Nasopharyngeal, b.) Oropharyngeal, and c.) Hypopharyngeal regions.

Mixed apnea is classified as a combination of central and obstructive apnea usually beginning with a central episode being immediately followed by an obstructive one.

Many devices have been developed to address the problem of sleep apnea. One such device is Continuous Positive Airway Pressure (CPAP) this technique involves wearing a mask tightly over the nose during sleep. Pressure from an air compressor forces air through the nasal passages and into the airway. This forced air creates a pneumatic splint, keeping the airway open and allowing the person to sleep normally. Though this technique is highly effective, this therapy is not for everyone. In fact, daily compliance by persons using CPAP is less than 50%. Furthermore, this technique has many drawbacks some of which are that it is uncomfortable, inconvenient, restricts the person's motion and dries out the mucosa. Further still, there is also a real concern of having reduced cardiac output and renal function.

Another approach to treating apnea is to surgically alter the person's breathing passages. The most effective surgical procedures for treating apnea is a tracheostomy which enjoys a 100% success rate because it completely bypasses all of the sites of the upper airway obstruction. Although it is rarely accepted by persons because many cannot accept the idea of permanent tracheostomy. A number of complications emerge with time, some of which are tracheal site infection, physiological problems, granulona formation, chronic irritation, uncontrolled secretions, bronchial infections and eventual stenosis.

A different surgical approach is nasal reconstruction. Many times a nasal obstruction causes a person to mouth breath, when you breath through your mouth the mandible rotates back and allows the base of the tongue to drift posteriorly and block the airway.

A still further surgical method that may be employed is uvulopalatopharyngoplasty (UPPP). This procedure enlarges the air space by excising redundant soft tissue of the palate, uvula, tonsils, posterior and lateral pharyngeal walls. This procedure can be quite successful at stopping snoring, most studies indicate that this method is approximately 50% effective.

In addition to the techniques and devices above, there is still another series of devices that have been developed to treat sleep apnea. These devices can be classified as dental appliances. Dental appliances may be in the form of a soft palate lift device and tongue retention devices.

Many types of tongue holding devices are known. For example, metallic or hard plastic clips are disclosed in the art, e.g., in U.S. Pat. No. 4,198,967—Dror and U.S. Pat. No. 3,809,094—Crook. However, these devices risk pain and injury to the tongue, and are particularly unsuited to self-administration. A less traumatic device designed for self-administration and for extended periods of use (i.e., overnight) is disclosed in U.S. Pat. Nos. 4,169,473 and 4,304,277, both to Samelson. The device disclosed in the Samelson patents evacuates air from a tongue holder and uses an imperforate structure in a device that is positioned by holding both dental arches in a locked position. Such a device, however, is detrimental to the normal bite relationship of the dental arches since it distorts the relationship of the upper and lower jaws. U.S. Pat. No. 4,196,724—Wirt discloses a tongue receptacle having a rearwardly converging configuration into which the tip of the tongue is wedged. However, the device disclosed in the Wirt patent causes pain, swelling and edema by concentrating an applied vacuum to a small area of the tip of the tongue. Furthermore, the requirement for an attachment to a vacuum-producing device such as the disclosed elastically contractible bellows is cumbersome and annoying to a sleeping user. U.S. Pat. No. 4,676,240—Gardy proposes a device that engages either the teeth or the gum arches to anchor the device in position. The tongue is received in a vacuum chamber and displaces the air therein. The tongue is sealed in the chamber by internal sealing ridges located on the inside of the vacuum chamber.

Another such tongue retention device is described in U.S. Pat. No. 5,373,859 Forney and shown in FIG. 6. The Forney device, as illustrated in FIG. 6, is designed to retain the tongue in a normal or extended position without undue discomfort for an extended period of time by holding the tongue securely in a housing by means of vacuum created within the device. The housing may then be positioned by holding it with the fingers or, in another embodiment, by an integral flange which rests against the face and permits self-application. The device uses a housing that is designed to form a seal with the tongue at its proximal portion, and diverging walls within the housing to limit other areas of contact with the tongue. The device also preferably uses an opening that is arcuate shaped and includes a soft conformable extension portion.

Shortcomings of these devices are that the device extends beyond the person's teeth and into the oral cavity. Additionally, the device cannot be custom fitted to each individuals anatomy because any modifications to the distal portion of the device will reduce the overall vacuum effect. Still further, many of these devices are constructed of thick non-yielding materials that when in use prove to be very uncomfortable to be worn for extended periods of time because the device will not conform to the users anatomy. Another shortcoming of many of these devices is that the portion of the device adapted to receive the person's tongue are not designed having a limited volume, thus the user may insert a greater amount of tissue into the device therefore resulting in great discomfort to the user. Lastly, many of the presently available devices further include stiffening means disposed within the device, many times the stiffening means is in the form of ribs disposed within the area adapted for receiving the person's tongue, thus when a vacuum is drawn to retain the device upon the person's tongue these stiffening ribs prove to be uncomfortable.

There remains a need for a device that can position a person's tongue in an extended manner to treat sleep apnea. It is therefore an object of this invention to provide a pliable device which comfortably holds a tongue using vacuum forces.

It is another object of the present invention to provide a device which may be comfortably worn while sleeping and which does not extend into the oral cavity of the person.

It is a further object of the present invention to provide a device which may be easily cleaned after use.

It is still a further object of the present invention to provide a device for retaining a person's tongue in an extended manner where the device does not require great manual dexterity to utilize.

BRIEF DESCRIPTION OF THE INVENTION

In accordance with one aspect of the present invention there is provided a device for retaining a tongue in a predetermined position, the device comprising, a flange having a first and second surface, the flange further including a protrusion extending from the first surface of said flange. The device further including an aperture formed through said first and second surfaces of said flange, wherein the protrusion covers the aperture, whereby the protrusion forms a hollow chamber, the hollow chamber being accessible through the aperture from the second side of the flange.

In accordance with another aspect of the present invention there is provided a device for retaining a tongue in a predetermined position, the device comprising, a flange having a first and second surface, an aperture disposed within the flange wherein the aperture further includes walls extending from the first surface of a flange, the walls forming a bulb protruding from the first surface of the flange, wherein the bulb forms a chamber in communication with the aperture and being adapted to receive a tongue.

In accordance with another aspect of the present invention there is provided a method of retaining a tongue in a predetermined position, the method comprising, forming a vacuum within a tongue retention device by squeezing the walls of an protrusion extending from a flange of the tongue retention device, inserting a tongue through an aperture formed in the flange, wherein the tongue is received by the protrusion, releasing the walls, thereby forming a vacuum within the protrusion; and positioning the tongue retention device between a user's lips and teeth.

DETAILED DESCRIPTION OF THE DRAWINGS

The invention will now be described in greater detail with reference to preferred embodiments illustrated in the accompanying drawings, in which like elements bear like numerals; and wherein.

DETAILED DESCRIPTION OF PREFERRED EMBODIMENTS

Figure 1:
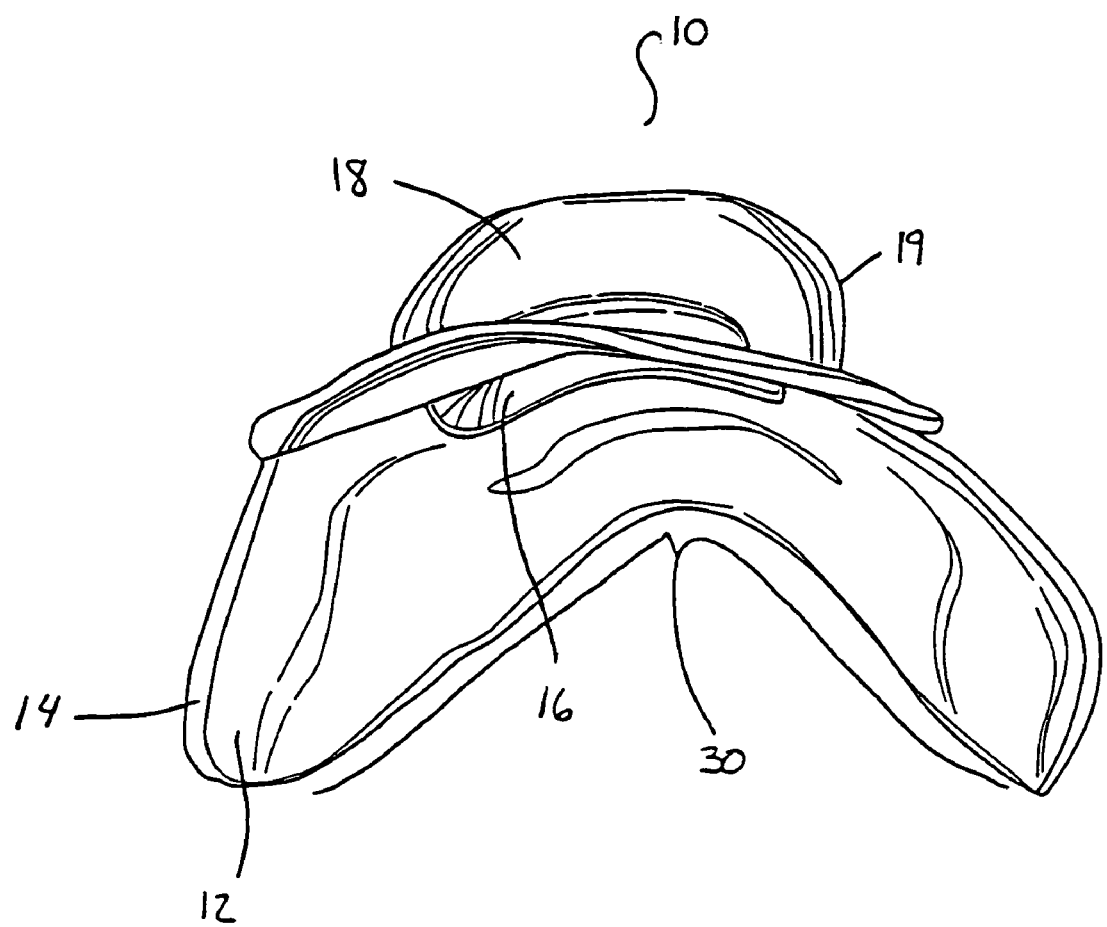
FIG. 1 is a top view of the tongue retention device of the present invention.
Figure 2:
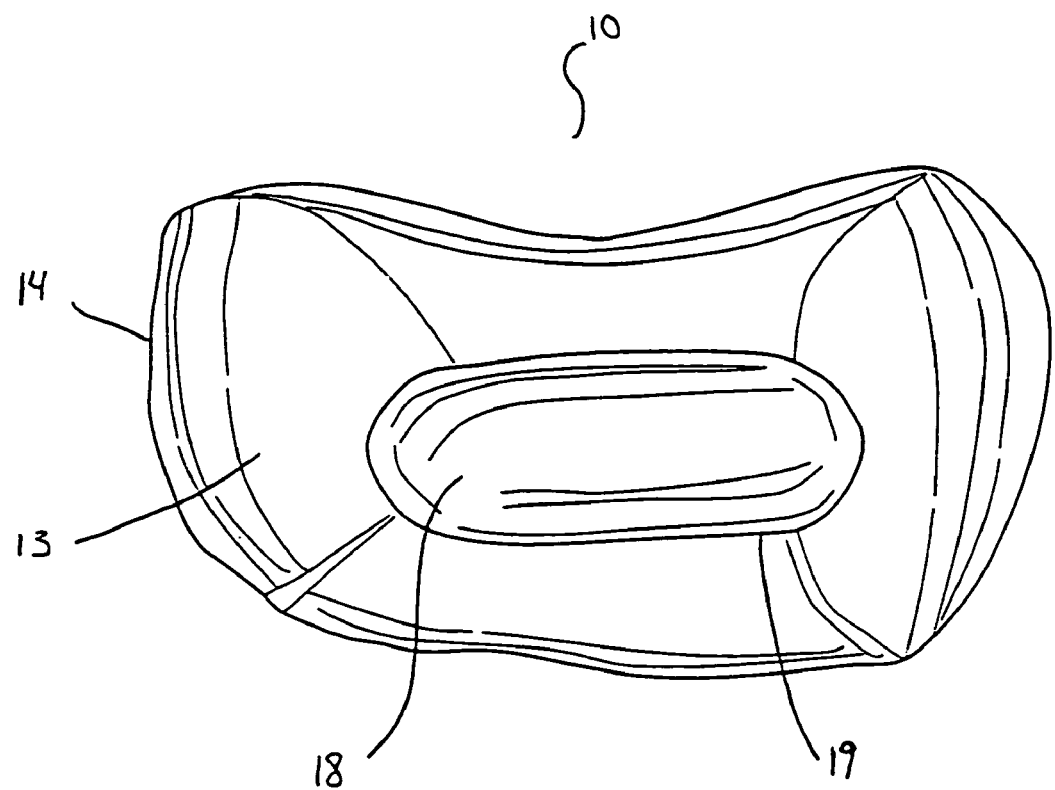
FIG. 2 is a front view of the tongue retention device illustrating a flange and a protrusion that extends from said flange.

Referring now FIG. 1 there is shown a tongue retention device 10 of the present invention. The tongue retention device 10 includes a flange 14, an aperture 16 and a bulb 18. The tongue retention device 10 is preferably formed as a unitary body wherein a soft pliable material is utilized in its construction. Such materials which may be utilized for the construction of tongue retention device 10 are polyvinylchloride, polyethylene, urethane, silicon or other similar bio-compatible materials. One such material that may be used to construct tongue retention device 10 of the present invention is referred to as "Sta-Vac sheet resin" which is available from a number of commercial manufacturers such as Buffalo Dental Manufacturing Company, 99 Lafayette Drive, Syosset, N.Y. 11791 USA.

The tongue retention device 10 may be formed having a constant thickness across it's entire cross section or alternatively, the cross sectional thickness may be varied according to design needs, preferably the tongue retention device 10 is formed having a thickness between about 0.010 inches and about 0.060 inches, more preferably between about 0.025 inches and about 0.040 inches.

As shown in FIGS. 1-5 tongue retention device 10 of the present invention may be formed by blow molding, injection molding, casting, vacuum forming or similar manufacturing procedures which will result in the formation of a one piece body.

Figure 3:
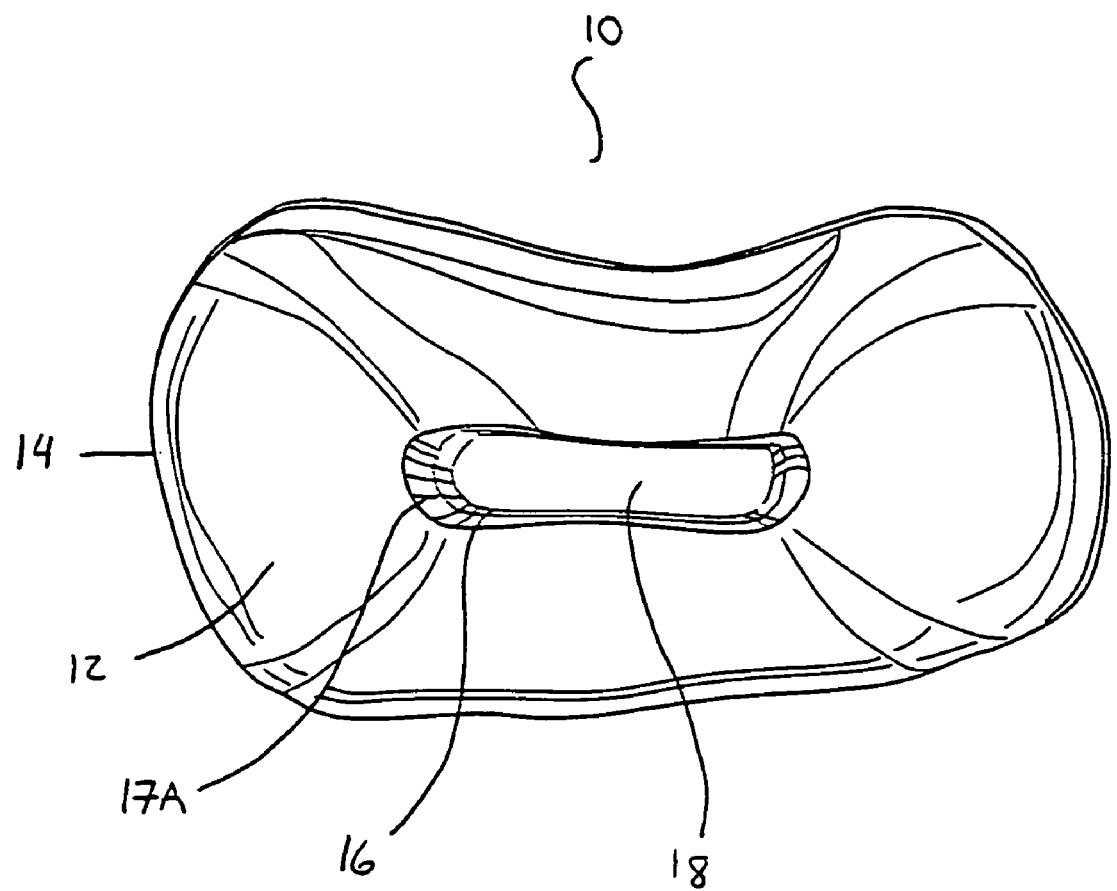
FIG. 3 is a back view of the tongue retention device illustrating the aperture formed in the flange, wherein the aperture is in communication with the protrusion.
Figure 4:
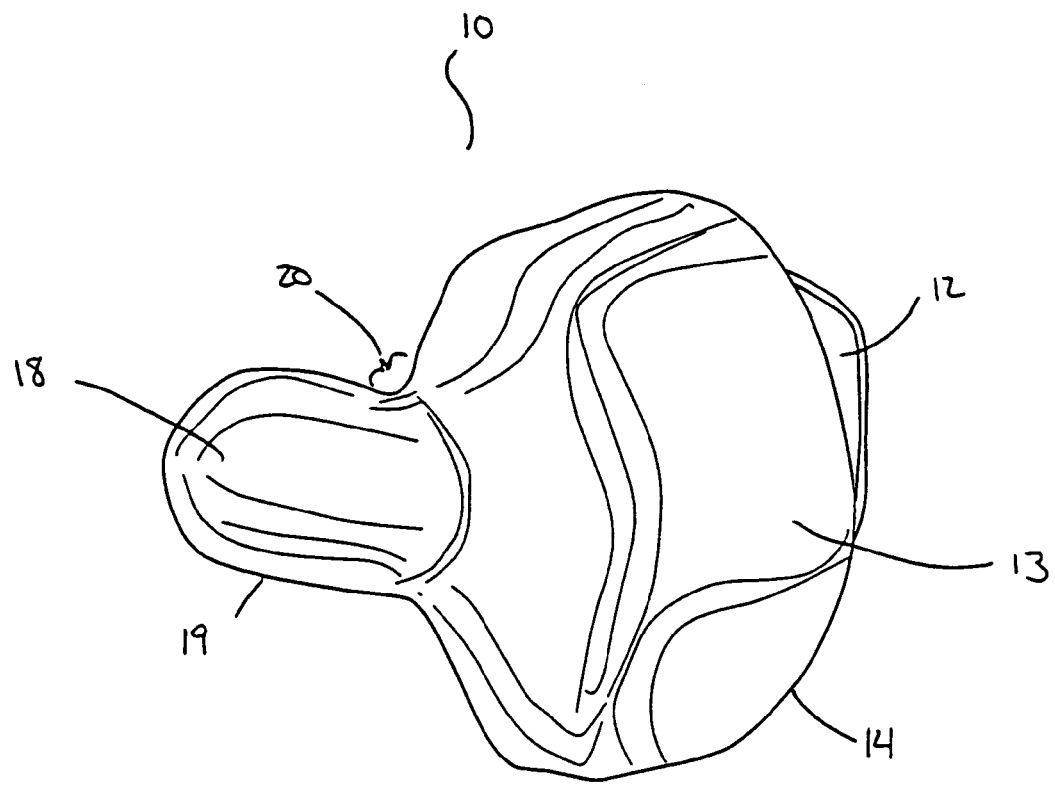
FIG. 4 is a side view of the tongue retention device.
Figure 5:
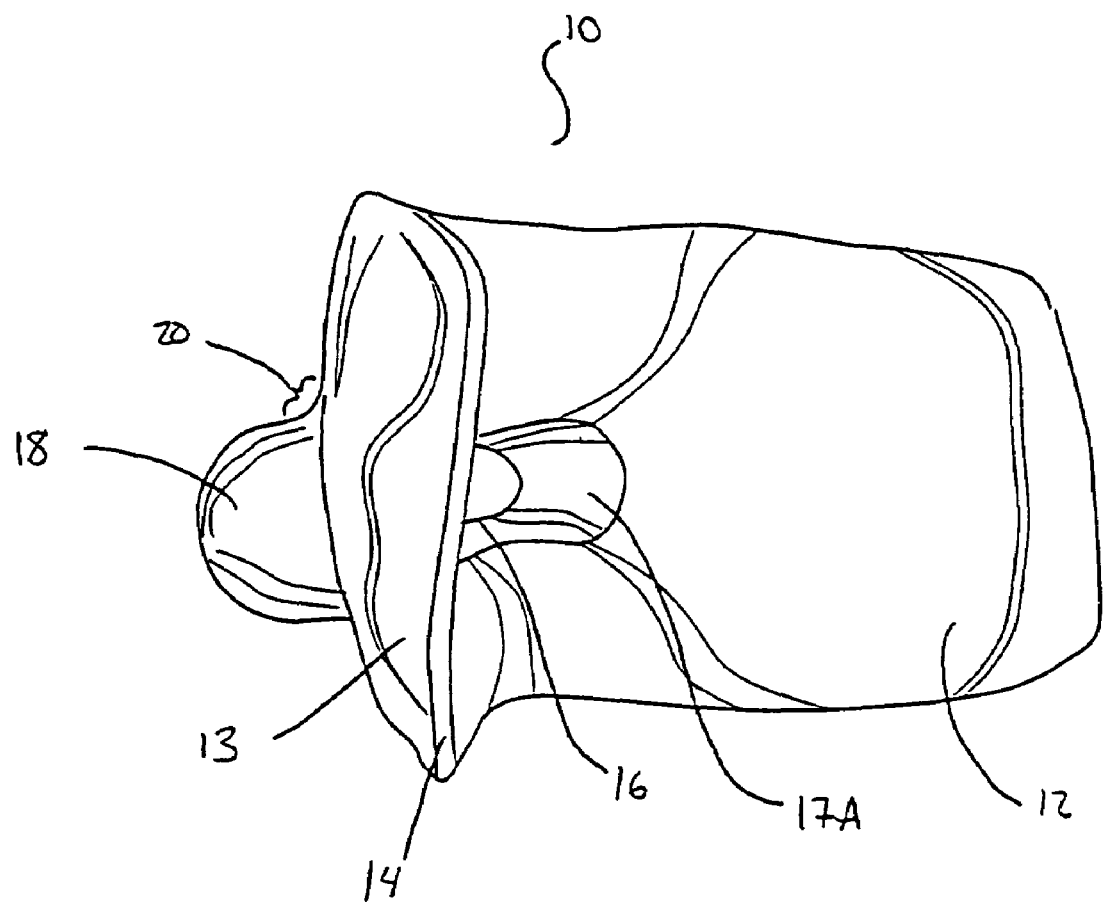
FIG. 5 is a perspective side view illustrating the flange, protrusion, and aperture.
Figure 6:
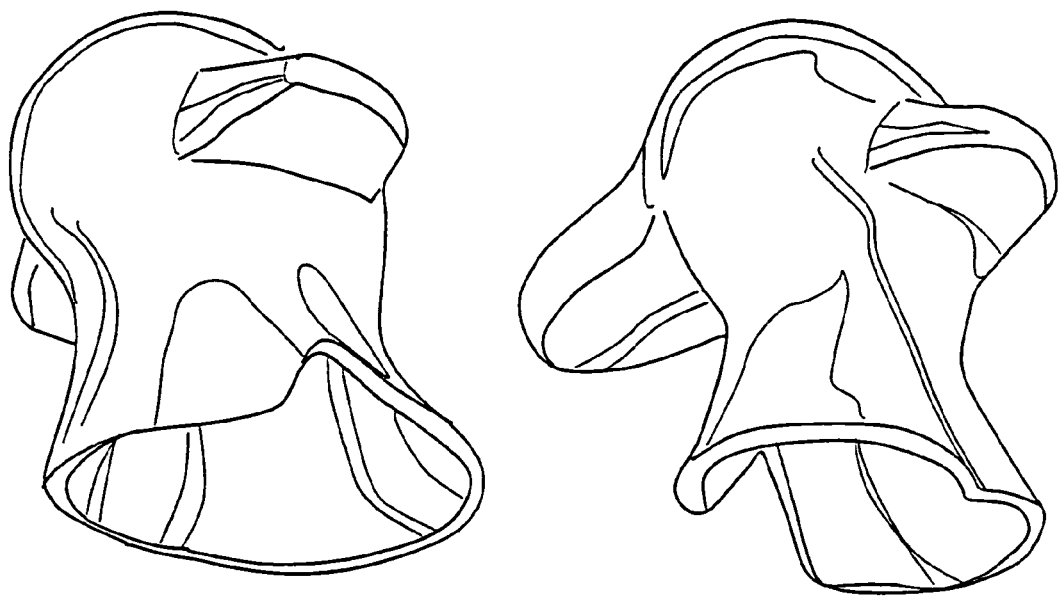
FIG. 6 is an illustration of a prior art tongue retention device.

Referring now to FIGS. 1, 3, and 5 there is shown the tongue retention device 10 of the present invention. As shown, the tongue retention device 10 includes a bulb 18. The bulb 18 is unitarily formed with flange 14 thereby forming a one piece tongue retention device 10 as described in detail above. As shown in FIGS. 4 and 5 the bulb is formed of walls 19 extending from the first surface 13 of the flange 14 forming the bulb 18. Additionally, as indicated by reference numeral 20, the bulb 18 forms a smooth transition with the first surface 13 of flange 14 thereby eliminating any sharp edges or surfaces which may contact the person's skin. Still further, the interior surfaces of bulb 18 are formed having a smooth surface finish. This smooth surface finish promotes easy cleaning in that bacteria cannot become lodged within any creases or openings in the surface. Additionally, the smooth surface provides a degree of comfort to the user.

As shown in FIGS. 1-5 the bulb 18 is formed being adapted to receive a person's tongue. The bulb 18 is also designed having a pre-determined volume such that only a pre-determined amount of the person's tongue will be received by the interior of the bulb 18. As shown in FIG. 3, the aperture 16 is designed having an elongated shape having radiused ends whereby the aperture may receive a person's tongue. The proximal area 17A of the aperture 16 is radiused accordingly so that the area 17A provides a smooth transition between the aperture 16 and the second surface 12. The distal area 17B (not shown) is also radiused to provide a smooth transition between the aperture 16 and the inner surface of the walls 19 of the bulb 18. In addition to the features above, the thickness of the material utilized to construct the tongue retention device 10 provides a sufficient amount of vacuum force within bulb 18 to retain the person's tongue therein but not a force that is to great as to cause pain and discomfort to the person.

Referring now to FIGS. 1-5 as shown, the flange 14 of the tongue retention device 10 further includes a curved portion 30. The curved portion 30 may be adjusted to fit the user's jaw line so that during use the device comfortably fits between the users teeth and lips. Still further, the overall size of the flange 14 may be adjusted by trimming to accommodate the sizes of different person's mouths. This feature also allows for the manufacture of a single size of the tongue retention device 10 thereby lowering overall production costs of the device. Alternatively, the tongue retention device 10 may be manufactured having multiple size variations in which both the flange and volume of the bulb 18 are adjusted accordingly.

In use, the bulb 18 of the tongue retention device 10 is gripped by the user and the user then places the tip of their tongue into the aperture 16 and the bulb 18 is squeezed to reduce the air volume within the bulb 18. By squeezing the bulb 18, air is forced out of the bulb past the person's tongue, when the force is released from the bulb 18, due to the resiliency of the material the bulb tries to return to it's uncompressed shape. In doing so, a vacuum is formed within the bulb because the tongue inserted into the aperture 16 provides a seal between the interior of the bulb 18 and the external atmospheric pressure. Thus, the tongue retention device 10 is thereby retained on the person's tongue. Alternatively, the person may insert their tongue through aperture 16 and into the bulb 18, after insertion they may then affix the tongue retention device by sucking back on the device and drawing air out of the bulb 18 thereby forming a vacuum therein. In utilizing either method, the user does not have to have a great deal of manual dexterity to affix the device to their tongue.

After affixing the tongue retention device to their tongue, the device is then positioned within the mouth, such that the second surface 12 of the flange 14 abuts the person's teeth and the first surface 13 of the flange 14 rests just behind the person's lips. Thus, in use, the tongue retention device 10 does not extend into the oral cavity of the person. Additionally, the tongue is accurately held into a pre-determined position. The position can be accurately reproduced with each use of the device, therefore the user is not required to adjust any parameter of the device between uses.

If needed, as described above, the overall size of the flange may be easily adjusted to accommodate a wide variety of geometries. For example, the flange may be trimmed down to fit a smaller mouth, or the curved portion 30 may be heat formed into a different curvature that may be more comfortable. In addition to providing treatment for sleep apnea, the tongue retention device of the present invention may also be utilized in applications regarding the treatment of bruxism (the grinding of teeth while sleeping) and thereby TJM muscle point for both those with teeth and without teeth.

Throughout the description above many advantages over the prior art are described. Such advantages include the limited volume of the bulb 18 thereby limits the volume of the tongue that will be retained by the tongue retention device 10. Still further, the tongue retention device 10 is formed of a material having a desired thickness such that overall the device remains pliable and resilient thereby resulting in a tongue retention device that is both comfortable and easy to use. Still further the design features of the present invention allow the tongue retention device 10 to be custom fitted for each application, thereby promoting comfort to the person while reducing overall manufacturing costs, alternatively, the design of the tongue retention device 10 allows for manufacture of various sizes. Also, unlike presently available devices, the tongue retention device 10 of the present invention does not protrude into the oral cavity. Lastly, the tongue retention device 10 of the present invention may be utilized in other applications such as the treatment of bruxism.

The foregoing description of certain preferred embodiments is set forth for the purpose of illustrating the principals of the invention. Since numerous alternative uses, modification and changes will readily occur to those skilled in the art, it is not desired to limit the invention to the exact construction and operation shown and described above, in the drawings and within the claims. Thus, all suitable modifications and equivalents that may be reported to will fall within the scope of the invention, which is defined by the appended claims.

The invention claimed is:

1. A device for retaining a tongue in a predetermined position, the device consisting essentially of:
   a single flange having a first and second surface, said single flange being sized and shaped to be comfortably received between a person's lips and frontal surface of a person's teeth or alveolar ridges if teeth are absent, said single flange further including a protrusion extending from said first surface of said single flange; and
   an aperture formed through said first and second surfaces of said single flange, wherein said protrusion covers said aperture, whereby said protrusion forms a hollow chamber, said hollow chamber being accessible through said aperture from said second side of said single flange;
   wherein said single flange and said protrusion comprise an integrally molded one-piece body.

2. The device according to claim 1, wherein said integrally molded one-piece body is formed by means of blow molding, injection molding, casting, or vacuum forming.

3. The device according to claim 1, wherein said aperture is adapted to receive a tongue.

4. The device according to claim 2, wherein said integrally molded one-piece body is constructed of a pliable material chosen from the group consisting of polyethylene, urethane, silicon, and polyvinylchloride.

5. The device according to claim 1, wherein a vacuum may be formed within said protrusion by compressing said protrusion and inserting a tongue into said aperture.

6. The device according to claim 1, wherein a vacuum is formed in said chamber by compressing said protrusion and inserting a tongue into said aperture.

7. A method of retaining a tongue in a predetermined position, the method comprising:
   forming a vacuum within a tongue retention device by squeezing walls of a protrusion extending from a flange of said tongue retention device;

inserting a tongue through an aperture formed in said flange, wherein said tongue is received by said protrusion;

releasing said walls, thereby forming a vacuum within said protrusion; and positioning said flange between a user's lips and frontal surface of said user's teeth such that the tongue retention device does not extend substantially past the user's teeth and into the user's oral cavity.

8. The method as claimed in claim 7, wherein said flange is positioned between a user's lips and frontal surface of said user's alveolar ridges if teeth are absent.

9. The device according to claim 1, wherein said integrally molded one-piece body is constructed of a material having a thickness between about 0.010 inches and about 0.060 inches.

10. The device according to claim 9, wherein said material has the thickness between about 0.025 inches and about 0.040 inches.

11. The device according to claim 1, wherein said integrally molded one-piece body is formed having a constant thickness across it's entire cross-section.

12. The device according to claim 1, wherein said single flange is adjustable to fit any size mouth.

13. The device according to claim 1, wherein said chamber has a pre-determined volume such that only a pre-determined amount of a person's tongue will be received in said chamber.

14. The device according to claim 1, wherein said chamber is sized and shaped to snugly receive a forward section of a person's tongue.

15. The device according to claim 1, wherein said aperture is elongated in shape for receiving a person's tongue.

16. A device for retaining a tongue in a predetermined position, the device consisting essentially of:

a single flange having a first and second surface, said single flange further including a protrusion extending from said first surface of said single flange; and an aperture formed through said first and second surfaces of said single flange, wherein said protrusion covers said aperture, whereby said protrusion forms a hollow chamber, said hollow chamber being accessible through said aperture from said second side of said single flange;

wherein said single flange is sized and shaped to be comfortably received between a person's lips and frontal surface of a persons teeth or alveolar ridges if teeth are absent.

17. The device according to claim 16, wherein said single flange is curved to fit a person's jaw line.

18. The device according to claim 16, wherein said single flange is constructed of a material having a thickness between about 0.010 inches and about 0.060 inches.

19. The device according to claim 18, wherein said material has the thickness between about 0.025 inches and about 0.040 inches.

20. The device according to claim 16, wherein said single flange and said protrusion comprise an integrally molded one-piece body.

21. The device according to claim 20, wherein said integrally molded one-piece body is formed by means of blow molding, injection molding, casting, or vacuum forming.

22. The device according to claim 16, wherein said aperture is adapted to receive a tongue.

23. The device according to claim 20, wherein said integrally molded one-piece body is constructed of a material selected from the group consisting of polyethylene, urethane, silicon, and polyvinylchloride.

24. A kit comprising:

a device for retaining a tongue in a pre-determined position consisting essentially of a bulb having a closed end and an open end, said bulb forming a hollow chamber for receiving a tongue through said open end, and a single flange extending outwardly from said open end, said single flange to be received between a person's lips and frontal surface of said person's teeth or alveolar ridges if teeth are absent; and instructions for use of said device comprising adjusting the overall size of said single flange to comfortably fit between a person's lips and frontal surface of said person's teeth.

25. The kit according to claim 24, wherein said adjustment of said single flange comprises trimming said single flange with a cutting device.

* * * * *